(12) United States Patent
Jackson et al.

(10) Patent No.: US 11,219,539 B2
(45) Date of Patent: Jan. 11, 2022

(54) DRY ABSORBENT LAYER SYSTEM

(71) Applicants: Nema Jackson, Berwyn, IL (US); Clousteen Jackson, Berwyn, IL (US)

(72) Inventors: Nema Jackson, Berwyn, IL (US); Clousteen Jackson, Berwyn, IL (US)

( * ) Notice: Subject to any disclaimer, the term of this patent is extended or adjusted under 35 U.S.C. 154(b) by 0 days.

(21) Appl. No.: 16/878,539

(22) Filed: May 19, 2020

(65) Prior Publication Data

US 2021/0100664 A1    Apr. 8, 2021

Related U.S. Application Data

(60) Provisional application No. 62/909,354, filed on Oct. 2, 2019.

(51) Int. Cl.
| | |
|---|---|
| A61F 2/78 | (2006.01) |
| A61L 15/28 | (2006.01) |
| A61L 15/58 | (2006.01) |

(52) U.S. Cl.
CPC ............ A61F 2/7812 (2013.01); A61L 15/28 (2013.01); A61L 15/58 (2013.01); *A61F 2002/785* (2013.01); *A61F 2002/7806* (2013.01); *A61L 2300/232* (2013.01); *A61L 2300/608* (2013.01)

(58) Field of Classification Search
CPC .............. A61F 2/7812; A61F 2002/785; A61F 2002/7806; A61L 2300/608; A61L 15/58; A61L 15/28; A61L 2300/232
See application file for complete search history.

(56) References Cited

U.S. PATENT DOCUMENTS

| | | | | |
|---|---|---|---|---|
| 3,600,717 | A * | 8/1971 | McKeehan | A61F 2/7812 602/61 |
| 5,452,525 | A * | 9/1995 | Miyauchi | A43B 17/102 36/44 |
| 6,362,387 | B1 * | 3/2002 | Carlson | A43B 7/1465 442/370 |
| 9,867,965 | B1 * | 1/2018 | Kantor | A61F 13/06 |
| 2011/0092935 | A1 * | 4/2011 | Hann | A61F 13/53708 604/367 |

FOREIGN PATENT DOCUMENTS

DE        202012005301 U1 *  6/2012  ........... A43B 1/0045

* cited by examiner

*Primary Examiner* — Elizabeth C Imani
(74) *Attorney, Agent, or Firm* — K&L Gates LLP

(57) ABSTRACT

The present invention relates to absorbent articles for solving the problem of stopping the excessive accumulations of sweat from building up inside a prosthetic liner. The four layers of materials include: a first layer of a cellulose pulp material having a thickness use for a desired absorbency, a second layer of a wicking cloth material having a thickness use for a desired absorbency, a third layer of a non-toxic double side adhesive tape material one side will stick to both layer, and a fourth layer that is the opposite side which are cover with paper material that can be peeled from the third layer to adhere the inside of a prosthetic liner base sheet to stop the excessive accumulation build-up of sweating.

20 Claims, 3 Drawing Sheets

DRY ABSORBENT LAYER SYSTEM

CROSS-REFERENCE TO RELATED APPLICATIONS

This application incorporates by reference and claims the benefit of priority to U.S. Provisional Application 62/909,354 filed on Oct. 2, 2019.

BACKGROUND OF THE INVENTION

The present invention relates generally to a disposable dry absorbent layered system. More specifically, it relates to an assortment of absorbent layers used for keeping a prosthetic liner dry.

Any discussion throughout the specification should in no way be considered as an admission that such is widely known or forms part of common general knowledge in the field. While there are designs of disposable absorbent articles relating to solving many of the problems in the field of medicine, industry, hygiene, and the household, there are no disposable dry absorbent article products that have been created in the prosthetic industry that can keep a prosthetic liner dry from the dangerous buildup of sweat inside the unpleasant, wet, thermal conditions found in a prosthetic liner.

Prosthetics liners are designed to be used directly against a user's skin, which results in excessive sweat accumulation inside the prosthetic liners that can be very uncomfortable, and known to be very possibly dangerous, for the user. For example, the user may feel like he or she is wearing a sweat suit against the skin where the prosthetic liner contacts the user's skin. The longer the moisture remains on the skin and in contact with the prosthetic liner, the greater chance for dangerous adverse health issues to develop. Once the top layer of skin (e.g., sheath) is soaked with sweat, the skin can become softer such that when friction occurs on the surface between the sheath, the damp skin can cause blisters or macerations. The compromised skin can become prone to develop infections which becomes very painful when left untreated, leading to further dangerous life-threatening infections and complications.

Further, in hot and humid conditions, sweat accumulates much faster inside the prosthetic liner. As a result of the sweating buildup, a user constantly needs to remove the prosthetic liner to wipe away excessive sweating from inside the liner throughout the day, even when other parts of the wear's body are not sweating. About 80% of user's are required to use a sock with their prosthetic liners in order to function against accumulation of sweat within their prosthetic liner.

When dangerous excessive sweat is present inside a prosthetic liner, the prosthetic liner can slip off of a user's limb, thereby increasing the danger and risk of further injury due to unsteady balance due to the dangerous excessive sweat buildup in the wet prosthetic liner. However, the use of a sock to prevent sweat buildup can alter the fit of the prosthetic liner, as well as cause chafing to the user due to the moisture and sweat buildup. When the fit is altered by the liner or sock, the user is susceptible to further injuries.

While there are many designs of disposable absorbent materials in the field of medicine, industry, hygiene, and household sectors, the prosthetic liners industry has failed to invent a method to this day for keeping a prosthetic liner dry and to solve the problem of excessive accumulation of sweat buildup inside of the wet, thermal environment found inside the prosthetic liner.

BRIEF SUMMARY OF THE INVENTION

The present system is directed to keeping a prosthetic liner dry using a disposable dry absorbent layered (DAL) system configured to provide an interface between an amputated limb and the prosthetic liner. Specifically, the present disclosure provides a disposable dry absorbent layered system to keep the inside of an otherwise wet prosthetic liner dry by preventing excessive sweat accumulation inside of a prosthetic liner (e.g., the wet thermal environment inside the prosthetic liner). Various examples of the systems and methods are provided herein.

The present disclosure provides a dry absorbent layered system that in one example includes a wicking cloth layer, a cellulose pulp layer, and an adhesive layer. In another example, the adhesive layer may include a non-toxic double-sided adhesive tape layer with a wax paper covering.

Specifically, the present system keeps otherwise wet prosthetic liners dry by preventing the excessive accumulation of sweat build-up inside any prosthetic liners. The present system can include four layers of materials including: (1) a first cellulose wood pulp material layer, (2) a second wicking cloth material layer, (3) a third non-toxic adhesive double side tape layer, and, optionally, (4) a fourth paper material layer covering the back (outer surface) of the third layer, wherein the paper layer can be peeled from third layer. Following the peeling of the fourth layer form the third layer, the product can be placed inside at the base on the surface inside a prosthetic liner to keep the inside of the liner dry.

Layers can be polymeric, or non-polymeric cellulose wood pulp, safe to humans, including layers of polymeric, or non-polymeric wicking cloth, safe to humans, or can have any combinations of polymeric layers thereof. As an example, while described in one example as a four-layer article, each layer itself may be one or more layers of material. In one example, the first cellulose wood pulp material layer may actually be multiple layers of cellulose wood pulp material.

In one example of the article, the first layer can be organic or non-organic cellulose pulp having the thickness for any needed absorbency, can be polymeric, non-polymeric materials, or combinations thereof, and is safe to humans. A second layer can be organic, or non-organic wicking cloth having the thickness for any needed absorbency, can be made from polymeric materials, non-polymeric materials, or combinations thereof, and is safe to humans. A third layer can be a non-toxic double side adhesive layer. All three layers can be bonded together to form the disposable dry absorbent layer system.

In some embodiments, the absorbent layer may be used adjacent the user's skin. In other examples, the wicking layer may be used adjacent the user's skin. It is also understood that each of the absorbent layer and the wicking layer may exhibit properties of the other, such that, for example, the wicking layer exhibits absorption properties and the absorption layer exhibits wicking properties. In fact, it is expected that each layer performs each function to a varying degree, as will be understood by those skilled in the art based on the disclosures provided herein.

The fourth layer can be a backing to the adhesive, the backing formed by paper material releasably covering the third layer. A user can peel off the fourth layer of the DAL system to expose the adhesive layer and then the article can be adhered at the base on the surface inside a prosthetic liner, wherein the sweat can be absorbed from a limb inside a prosthetic liner, wherein the DAL system prevents the excessive accumulation of sweat build-up inside a prosthetic liner.

An advantage of the present disposable dry absorbent layered system is that the system can keep a prosthetic liner dry, absorbing sweat and dissipating heat from a limb, preventing the accumulation of excess fluid buildup inside of a prosthetic.

For example, the present disposable dry absorbent layers system has a combination of absorbent layer materials to absorb sweat and dissipate heat simultaneously to prevent the accumulation of excess sweat from building up inside what would otherwise be a wet thermal environment inside a prosthetic liner.

A further advantage of the present dry absorbent layered system is that it maintains a dry environment for a user of a prosthetic liner, thereby enabling normal mobile activity by the user.

Another advantage of the present dry absorbent layered system is that the system helps to minimize non-medical and medical issues that are commonly caused by excessive buildup of sweat inside the prosthetic liner.

Another advantage of the present dry absorbent layered system is that the system can be manufactured to embody any preferred style, design, and fashion, while being made from various materials intended to assist in keeping a wet prosthetic liner dry, while stopping excessive accumulation build-up of sweat inside a prosthetic liner.

Without the present DAL system in place, excessive moisture buildup within the prosthetic liner creates an environment that is idea for the growth of microbes that can result in a number of adverse health issues. The present dry absorbent layered system helps to keep a wet prosthetic liner dry, helps reduce or prevent skin breakdown, and helps to reduce or prevent inflammation, thereby reducing or preventing rashes and infections of the skin in contact with the prosthetic liner.

Another advantage of the present DAL system, when the DAL system is placed at the base on the surface inside a prosthetic liner, it helps to reduce both non-medical and medical issues that otherwise can create a very dangerous environment for the user (e.g., by reducing the buildup of sweat dripping down from a limb being worn in a wet thermal environment inside a prosthetic liner).

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

The present disclosure provides a dry absorbent layered system including a wicking cloth layer, a cellulose pulp layer, and an adhesive layer to assist in minimizing the accumulation of sweat and other moisture on the inside of a prosthetic liner, helping to prevent the growth of microbes and minimize other adverse effects that would result from moisture build up. A method is disclosed to utilize the disposable dry absorbent layered system in a prosthetic liner to assist in minimizing the accumulation of sweat and other moisture on the inside of the prosthetic liner, helping to prevent the growth of microbes and minimize other adverse effects that would result from moisture build up.

Figure 1:
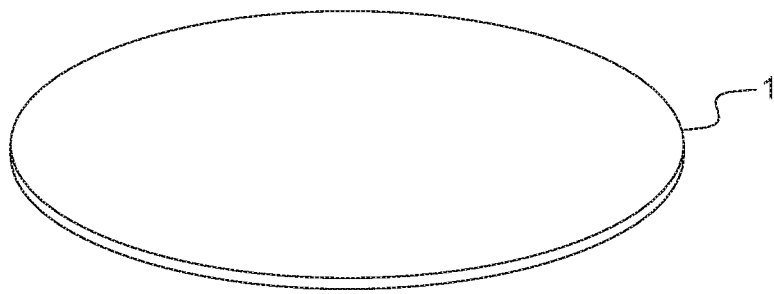
FIG. 1 is a front-top perspective view of a first layer, an organic, or non-organic circular cellulose pulp absorbent material.

FIG. 1 shows an example of an absorbent material layer 1. The absorbent material layer 1 can include organic and/or non-organic material. In an example, the absorbent material layer 1 can include organic and/or non-organic cellulose pulp having a thickness selected for the desired magnitude of absorbency. In an example, the absorbent material layer 1 can include an absorbent cellulose wood fiber reinforced with polypropylene (e.g., a polypropylene plastic resin, conventionally known as plastic number 5), which may be recyclable. Alternatively, or in addition to, the absorbent material layer 1 can include others absorbent fabrics and/or polymers that are safe to humans. The absorbent material layer 1 can also include organic and/or non-organic cotton materials. In an example, the absorbent material layer 1 can include reinforced absorbent cotton polymeric materials that are safe to humans. In one example, the absorbent material layer 1 may be of a thickness between and including 0.1 to 0.4 mm (e.g., 0.3 mm).

In an example, the absorbent material layer 1 can include cellulose acetate, cellulose triacetate, cellulose propionate, cellulose acetate propionate, cellulose acetate butyrate, nitrocellulose, cellulose sulfate, methylcellulose, ethylcellulose, ethyl methyl cellulose, hydroxyethyl cellulose, hydroxypropyl cellulose, hydroxyethyl methyl cellulose, hydroxypropyl methyl cellulose, ethyl hydroxyethyl cellulose, carboxymethyl cellulose, or combinations thereof. In an example, the absorbent material layer 1 can include one or more organic polymers, thermoplastic polymers, celluloids, cellophanes, cotton, rayon, paper, hemp, or combinations and sub-combinations thereof, as will be recognized by those skilled in the art based on the teachings herein.

Figure 2:
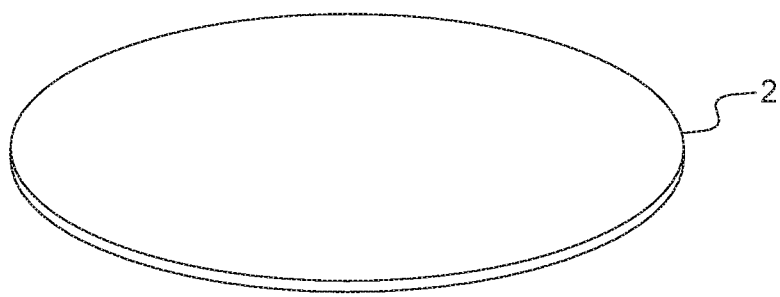
FIG. 2 is a front-top perspective view of a second layer of an organic, or non-organic circular wicking cloth absorbent material.

FIG. 2 shows an example of a wicking material layer 2. The wicking material layer 2 can be made of organic and/or non-organic wicking cloth material having a thickness for desired absorbency. In an example, the wicking material layer 2 can include polyester, polypropylene, wool, spandex, bamboo, nylon, silk, or combinations and sub-combinations thereof, as will be recognized by those skilled in the art based on the teachings herein. In an example, the wicking material layer 2 can be identical to the absorbent material layer 1, with each of the absorbent material layer 1 and the wicking material layer 2 contributing to the absorption and wicking of moisture from the surface of the dry absorbent layered system 5.

Figure 3:
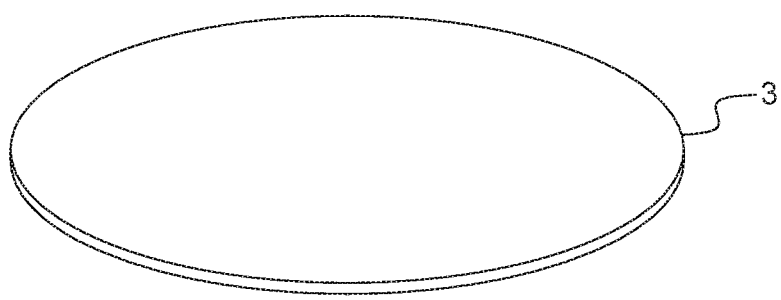
FIG. 3 is a front-top perspective view of a third layer, a non-toxic, double-sided adhesive material.

FIG. 3 shows an example of an adhesive material layer 3. The adhesive material layer 3 may be, for example, a non-toxic, double-side adhesive tape that holds the absorbent material layer 1 and the wicking material layer 2 together while attaching them to the inner surface 8 of a prosthetic liner 10 (see FIGS. 5 and 7). As shown in FIG. 6, the first side of the adhesive material layer 3 can be attached to the wicking material layer 2. In the example shown in FIG. 6, the first side of the adhesive material layer 3 can adhere to both the wicking material layer 2 and a portion of the absorbent material layer 1. For example, as shown in FIG. 6, the diameter of the absorbent material layer 1 and the adhesive material layer 3 may be greater than the diameter of the wicking material layer 2. As a result, the first side of the adhesive material layer 3 can adhere to the portion of the absorbent material layer 1 that extends beyond the diameter of the wicking material layer 2.

Figure 4:
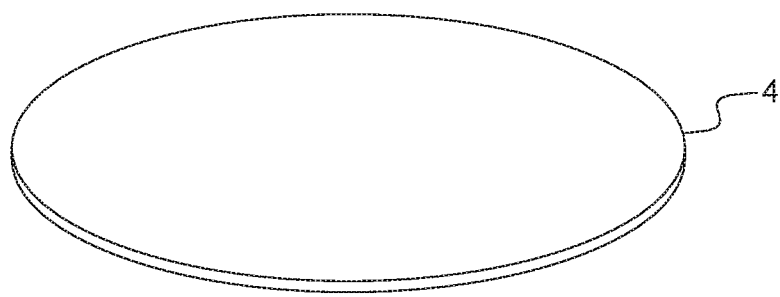
FIG. 4 is a front-top perspective view of the removable backing for the adhesive third layer.

As further shown in FIG. 6, a second side of the adhesive material layer 3, opposite the first side of the adhesive material layer 3, can be covered with a removable backing layer 4, shown in FIG. 4. The removable backing layer 4 may be formed from any material appropriately protective of the adhesive in the adhesive material layer 3 and yet easily removeable for use. In some example, the removable backing layer 4 may comprise a wax paper, linen layer, etc. When the removable backing layer 4 is peeled from the adhesive material layer 3 to expose the adhesive, the adhesive material layer 3 can adhere the dry absorbent layered system 5 to the base surface inside a prosthetic liner 10, as shown in FIGS. 5 and 7.

The dry absorbent layered system 5 can be any suitable size and shape to use in a prosthetic liner 10. For example, the absorbent material layer 1 may be circular and made of an organic, or non-organic, absorbent, cellulose pulp material having approximately a 4" diameter. The wicking material layer 2 may be circular and made of an organic, or non-organic, wicking cloth material having approximately a 3¾" diameter. The adhesive material layer 3 may be circular and made of a non-toxic, adhesive, double-sided material having approximately a 4" diameter. The removable backing layer 4 may be approximately a 4" diameter circle covering the outer surface of the adhesive material layer 3 to be peeled off to expose the adhesive material layer 3 when ready to use.

Figure 5:
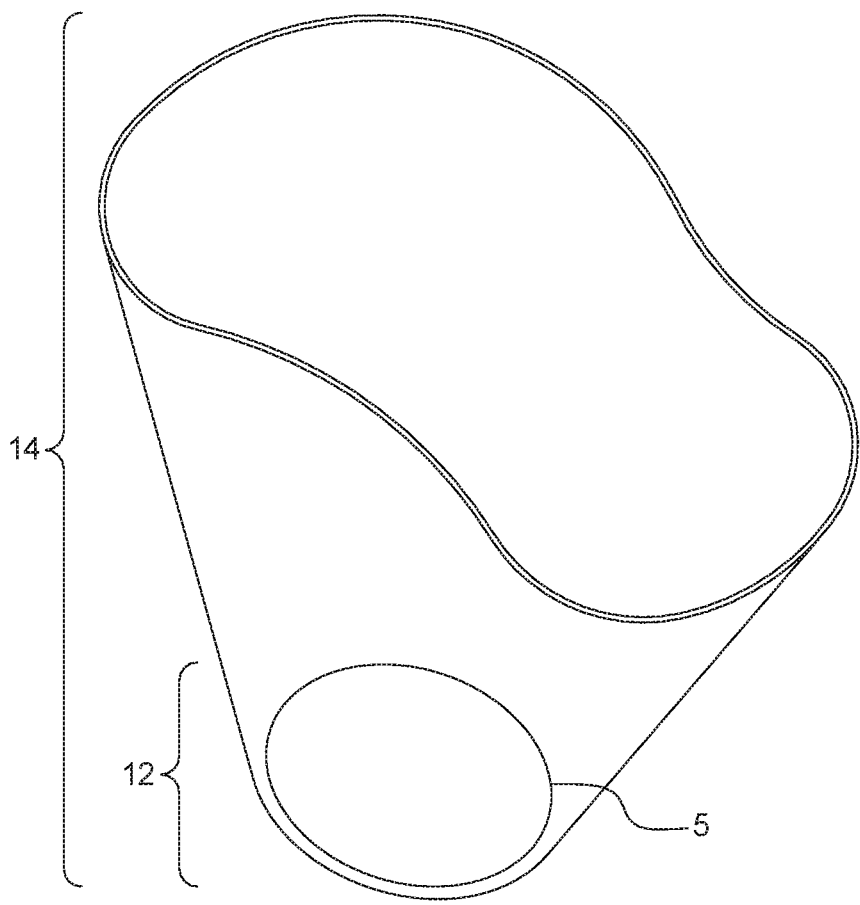
FIG. 5 is a front-top perspective view showing the DAL system adhered at the base on the lower surface inside of a prosthetic liner.
Figure 6:
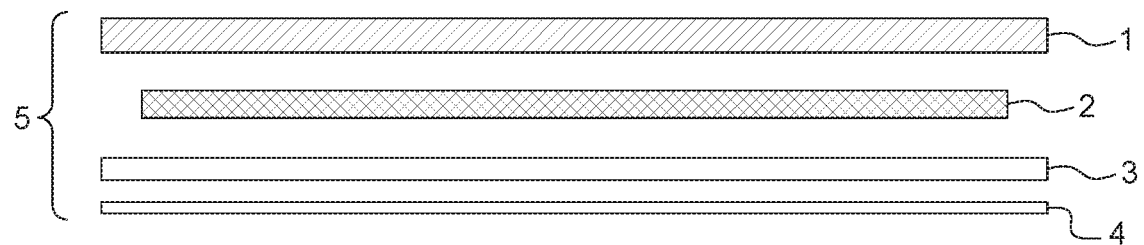
FIG. 6 is a front side elevational view showing the first layer, the second layer, the third layer, and the fourth layer, wherein the double-sided adhesive third layer adheres to each of the first layer, the second layer, and the fourth layer.
Figure 7:
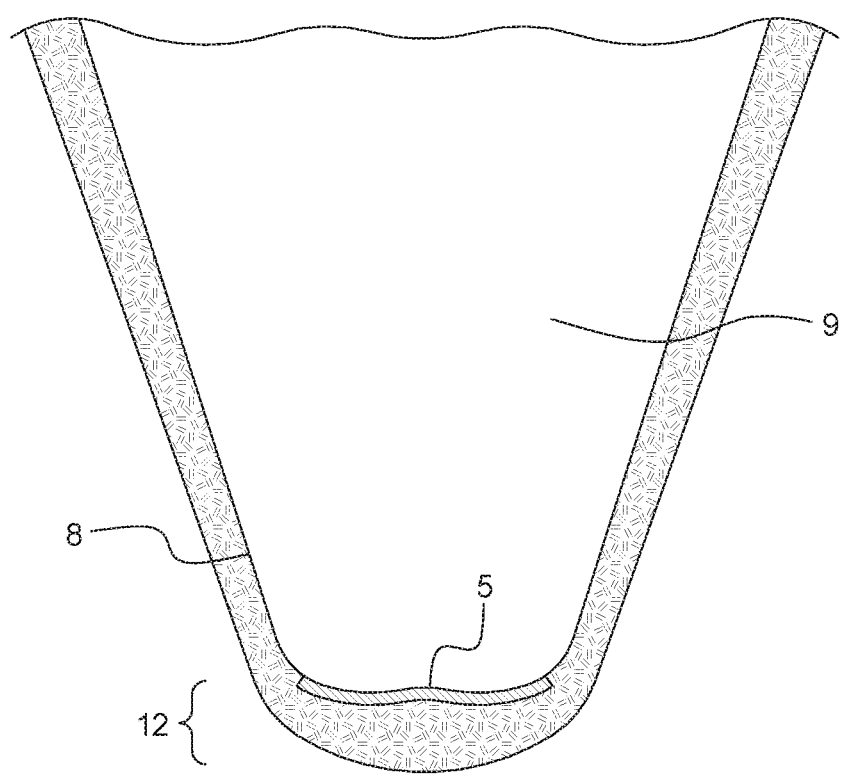
FIG. 7 is a cross-sectional view of the layered system in use in with a prosthetic liner.

As shown in FIGS. 1-6, the dry absorbent layered system 5 can be used in conjunction with a prosthetic liner 10. For example, the dry absorbent layered system 5 can include an absorbent material layer 1 of organic or non-organic cellulose pulp material having thickness for a desired absorbency, a wicking material layer 2 of organic or non-organic wicking cloth material having thickness for a desired absorbency and/or wicking properties, an adhesive material layer 3 comprising a non-toxic, double-sided adhesive material to adhere to and cover the wicking material layer 2. Further, the adhesive material layer 3 can adhere to the absorbent material layer 1, as shown in FIG. 6, which illustrates how the adhesive material layer 3 can bond with the absorbent material layer 1 and the wicking material layer 2. The outer surface of the adhesive material layer 3 (i.e., the surface not in contact with the absorbent material layer 1 and the wicking material layer 2) can be covered by a removable backing layer 4, such as a wax paper covering that, when peeled off, enables the dry absorbent layered system 5 to adhere to a base 12 inside a bottom of a prosthetic liner 10, as shown in FIG. 5. In other words, after the removable backing layer 4 (e.g., paper, etc.) is peeled from the adhesive material layer 3, the disposable dry absorbent layered system 5 can be then adhered to the base 12 of the surface inside of a prosthetic liner 10.

The present dry absorbent layered system 5 is to be used with a prosthetic liner 10. The prosthetic liner 10 can include a body 14 extending from a base 12, wherein the prosthetic liner 10 has an opening at the extend end of the body 14 for receiving a limb of a user. The prosthetic liner 10 used with the dry absorbent layered system 5 can be a standalone prosthetic liner 10 and/or be incorporated into a prosthetic. The prosthetic liner 10 can be custom made for particular users and prosthetics or may be an off-the-shelf item.

The prosthetic liner 10 can be made of any suitable material. For example, the prosthetic liner 10 can include any suitable organic fabric, polymeric material, silicone, urethane, thermosetting materials, or combinations and sub-combinations thereof, as will be recognized by those skilled in the art based on the teachings herein.

As shown in FIG. 6, the dry absorbent layered system 5 includes a combination of dry absorbent layers (DAL) used to keep a prosthetic liner 10 dry, by absorbing the constant accumulation of moisture build-up from a wearer's limb. Accordingly, the dry absorbent layered system 5 assists in preventing excessive accumulation of sweat build-up inside a prosthetic liner 10.

As shown in FIG. 7, the dry absorbent layered system 5 can absorb the sweat from a limb 9, while helping to dissipating the heat created inside a prosthetic liner 10. Without the dry absorbent layered system 5 provided herein, a user would need to change his or her prosthetic liner every three to four hours to keep the liner 10 dry, limit the growth of bacteria, prevent unwanted odor, and prevent irritating the limb 9. With the dry absorbent layered system 5 in place within the prosthetic liner 10, the user can wear the prosthetic liner 10 can be worn for longer periods of time before needing to be swapped out for a dry replacement. The dry absorbent layered system 5 is particularly useful in stopping the accumulation of excessive build-up of sweat inside a prosthetic liner 10, which assists in preventing skin breakdown, irritation, inflammation, rashes, etc. In particular, the use of the dry absorbent layered system 5 in hot and humid weather, and other time in which there would otherwise be excessive sweat accumulation, can lead to a much more comfortable, safe, and hygienic experience for users of prosthetics.

As described above, the dry absorbent layered system 5 may be made in various shapes and sizes. Most of the examples provided herein are shaped as circular disks, but the dry absorbent layered system 5 may be a square, a rectangle a triangle, etc. In an example, the dry absorbent layered system 5 can include a 3" to 5" (e.g., 4") diameter circular absorbent material layer 1 made of organic or non-organic cellulose pulp absorbent material having thickness to provide for a desired degree of absorbency, and a 2" to 4" (e.g., 3¾") diameter circular wicking material layer 2 made of organic or non-organic wicking cloth absorbent material having thickness to provide for a desired degree or wicking and absorbency. The dry absorbent layered system 5 can include a 3" to 5" (e.g., 4") diameter circular adhesive material layer 3 made of a non-toxic, double-sided adhesive material.

In some examples, such as the embodiment shown in FIG. 6, the adhesive material layer 3 is adhered to both the absorbent material layer 1 and the wicking material layer 2. In other examples, the layers may be adhered or otherwise joined to each other using other adhesive mechanisms or techniques as will be recognized by those skilled in the art. For example, there may be an additional tie layer (not shown) that adheres or otherwise joins the absorbent material layer 1 and the wicking material layer 2 to each other.

As shown in FIG. 7, when the removable backing layer 4 is removed from the adhesive material layer 3, the dry absorbent layered system 5 can be adhered at the base 12 on the surface inside a prosthetic liner 8.

With further reference to FIG. 7, under typical use conditions, it generally takes about ten to twenty minutes for the sweat from a limb 9 that is inside the prosthetic liner 8 to begin to saturate the prosthetic liner 8. In the example shown in FIG. 7, the limb 9, may be an upper leg from which the sweat collects at the base 12 of the prosthetic liner 8. Accordingly, the dry absorbent layered system 5 located at the base 12 of the prosthetic liner 8 collects and absorbs the excess sweat, providing for an environment which helps to keep the prosthetic liner 8 dry and help maintain the health and wellness of the limb 9.

While primarily described herein with reference to the layer of the dry absorbent layered system 5 to be positioned adjacent to the limb 9 as being the absorbent material layer 1 and the wicking material layer 2 being the layer sandwiched between the absorbent material layer 1 and the adhesive material layer 3, it is understood that certain embodiments of the dry absorbent layered system 5 may swap the materials used in these layers such that the layer closest to the limb 9 may instead be the wicking material layer 2, which wicks the moisture away from the user's limb 9 to an inner layer functioning as the absorbent material layer 1. In such embodiments, the size and shape of the absorbent material layer 1 and the wicking material layer 2 may also be swapped, with the absorbent material layer 1 being a smaller diameter than the wicking material layer 2.

It should be noted that various changes and modifications to the embodiments described herein will be apparent to those skilled in the art. Such changes and modifications may be made without departing from the spirit and scope of the present invention and without diminishing its attendant advantages. For example, various embodiments of the systems and methods may be provided based on various combinations of the features and functions from the subject matter provided herein.

We claim:

1. An absorbent system for use on a limb comprising:
   a combination of a prosthetic liner and a disposable dry absorbent layer system, the disposable dry absorbent layer system configured to be positioned within the prosthetic liner, the disposable dry absorbent layer system comprising:
   an absorbent material layer including a cellulose pulp material;
   a wicking material layer including a wicking cloth material, wherein a diameter of the wicking material layer is less than a diameter of the absorbent material layer; and
   an adhesive material layer including a non-toxic, double-sided adhesive material having a diameter greater than the diameter of the wicking material layer;
   wherein the wicking material layer is positioned between the absorbent material layer and the adhesive material layer;
   wherein a first side of the adhesive material layer is adhered to an outer perimeter of the absorbent material layer to enclose the wicking material layer and form the disposable dry absorbent system; and
   wherein a second side of the adhesive material layer is configured to adhere to the prosthetic liner.

2. The system of claim 1, wherein the absorbent material layer includes cellulose wood pulp material.

3. The system of claim 1, wherein the absorbent material layer has a diameter between, and including, 3 to 5 inches.

4. The system of claim 1, wherein the wicking material layer has a diameter between, and including, 2.5 to 4.5 inches.

5. The system of claim 1, wherein the adhesive material layer has a diameter between, and including, 3 to 5 inches.

6. The system of claim 1, wherein the absorbent material layer has a diameter of 4 inches, wherein the wicking material layer has a diameter of 3.75 inches, and wherein the adhesive material layer has a diameter of 4 inches.

7. The system of claim 1, further comprising a prosthetic liner, wherein the prosthetic liner includes a base and a wall extending from the base, wherein a second side of the adhesive material layer is positioned along the base of the prosthetic liner.

8. The system of claim 1, further comprising a prosthetic liner, wherein the prosthetic liner includes a base and a wall extending from the base, wherein a second side of the adhesive material layer is adhered to an inner surface of the base of the prosthetic liner.

9. The system of claim 1, further comprising a removable backing layer covering a second side of the adhesive material layer, wherein upon removal of the removable backing layer, an adhesive surface of the second side of the adhesive material layer is exposed.

10. An absorbent system for use on a limb comprising:
    a combination of a prosthetic liner and a disposable dry absorbent layer system, the disposable dry absorbent layer system configured to be positioned within the prosthetic liner, the disposable dry absorbent layer system comprising:
    an absorbent material layer including a cellulose pulp material;
    a wicking material layer including a wicking cloth material, wherein a diameter of the wicking material layer is greater than a diameter of the absorbent material layer, and wherein the wicking layer exhibits wicking properties; and
    an adhesive material layer including a non-toxic, double-sided adhesive material having a diameter greater than the diameter of the absorbent material layer;
    wherein the absorbent material layer is positioned between the wicking material layer and the adhesive material layer;
    wherein a first side of the adhesive material layer is adhered to an outer perimeter of the wicking material layer to form the disposable dry absorbent system; and
    wherein a second side of the adhesive material layer is configured to adhere to the prosthetic liner.

11. The system of claim 10, wherein the wicking material layer has a diameter between, and including, 3 to 5 inches.

12. The system of claim 10, wherein the absorbent material layer has a diameter between, and including, 2.5 to 4.5 inches.

13. The system of claim 10, wherein the adhesive material layer has a diameter between, and including, 3 to 5 inches.

14. The system of claim 10, wherein the wicking material layer has a diameter of 4 inches, wherein the absorbent material layer has a diameter of 3.75 inches, and wherein the adhesive material layer has a diameter of 4 inches.

15. The system of claim 10, further comprising a removable backing layer covering a second side of the adhesive material layer, wherein upon removal of the removable backing layer, an adhesive surface of the second side of the adhesive material layer is exposed.

16. The system of claim 10, further comprising a prosthetic liner, wherein the prosthetic liner includes a base and a wall extending from the base, wherein a second side of the adhesive material layer is adhered to an inner surface of the base of the prosthetic liner.

17. A method of preventing moisture buildup between a user's limb and a prosthetic, the method comprising:
providing a combination of a prosthetic liner and a disposable dry absorbent layer system, wherein the prosethetic liner is received by the prosthetic, wherein the prosthetic liner includes an internal liner surface, wherein the disposable dry absorbent layer system has an area that is less than an area of the internal liner surface and comprises:
an absorbent material layer including a cellulose pulp material;
a wicking material layer including a wicking cloth material; and
an adhesive material layer including a non-toxic, double-sided adhesive material;

applying the adhesive material layer of the disposable dry absorbent layer system to the internal liner surface of the prosthetic liner;
fitting the prosthetic liner over the user's limb such that the disposable dry absorbent layer system is positioned between the user's limb and the prosthetic liner; and
securing the user's limb within the prosthetic such that moisture accumulating between the user's limb and the prosthetic is absorbed by the disposable dry absorbent layer system.

18. The method of claim 17,
wherein a diameter of the wicking material layer is greater than a diameter of the absorbent material layer; and
wherein the adhesive material layer has a diameter greater than the diameter of the absorbent material layer, wherein the absorbent material layer is positioned between the wicking material layer and the adhesive material layer, wherein a first side of the adhesive material layer is adhered to an outer perimeter of the absorbent material layer to form the disposable dry absorbent system.

19. The method of claim 17,
wherein a diameter of the wicking material layer is less than a diameter of the absorbent material layer; and
wherein the adhesive material layer has a diameter greater than the diameter of the wicking material layer, wherein the wicking material layer is positioned between the absorbent material layer and the adhesive material layer, wherein a first side of the adhesive material layer is adhered to an outer perimeter of the absorbent material layer to form the disposable dry absorbent system.

20. The method of claim 17, wherein the disposable dry absorbent layer system is adhered to a base surface of the internal liner surface of the prosthetic liner.

* * * * *